(12) United States Patent
Kim et al.

(10) Patent No.: US 10,446,069 B2
(45) Date of Patent: Oct. 15, 2019

(54) DISPLAY DEVICE

(71) Applicant: Samsung Display Co., Ltd., Yongin-Si, Gyeonggi-Do (KR)

(72) Inventors: Hyunwoong Kim, Gwangmyeong-si (KR); Seung-kyu Lee, Asan-si (KR); Kwang-min Kim, Seoul (KR); Jongwon Park, Asan-si (KR)

(73) Assignee: Samsung Display Co., Ltd. (KR)

( * ) Notice: Subject to any disclaimer, the term of this patent is extended or adjusted under 35 U.S.C. 154(b) by 0 days.

(21) Appl. No.: 16/228,679

(22) Filed: Dec. 20, 2018

(65) Prior Publication Data

US 2019/0279543 A1 Sep. 12, 2019

(30) Foreign Application Priority Data

Feb. 8, 2018 (KR) .......................... 10-2018-0015829

(51) Int. Cl.
*G09G 3/00* (2006.01)
*G01N 21/958* (2006.01)
*H05K 1/02* (2006.01)

(52) U.S. Cl.
CPC .......... *G09G 3/006* (2013.01); *G01N 21/958* (2013.01); *H05K 1/028* (2013.01); *H05K 1/0269* (2013.01); *G09G 2310/0267* (2013.01)

(58) Field of Classification Search
CPC .......... G09G 3/006; G09G 2310/0267; G01N 21/958; H05K 1/0269; H05K 1/028
See application file for complete search history.

(56) References Cited

U.S. PATENT DOCUMENTS

| | | | |
|---|---|---|---|
| 7,893,441 B2 | 2/2011 | Hong et al. | |
| 8,400,437 B2 | 3/2013 | Kim et al. | |
| 9,768,068 B2 | 9/2017 | Choi et al. | |
| 9,875,676 B2 | 1/2018 | Byun et al. | |
| 9,928,768 B2 | 3/2018 | Kim et al. | |
| 2014/0203835 A1* | 7/2014 | Ro | G09G 3/006 324/760.02 |
| 2016/0247436 A1 | 8/2016 | Lee et al. | |
| 2018/0158741 A1 | 6/2018 | Kim et al. | |

FOREIGN PATENT DOCUMENTS

| | | |
|---|---|---|
| KR | 10-1296907 B1 | 8/2013 |
| KR | 10-1362015 B1 | 2/2014 |
| KR | 10-2016-0102644 A | 8/2016 |
| KR | 10-2016-0139122 A | 12/2016 |
| KR | 10-2016-0148834 A | 12/2016 |
| KR | 10-2017-0015698 A | 2/2017 |
| TW | 201822347 A | 6/2018 |

\* cited by examiner

*Primary Examiner* — Jamil Ahmed
(74) *Attorney, Agent, or Firm* — Innovation Counsel LLP

(57) ABSTRACT

A display device includes a display panel, a first inspection line, a second inspection line, and an inspection circuit controlling a connection between the first inspection line and a first pixel group and a connection between the second inspection line and the second pixel group. The inspection circuit includes a switching part including a first switching part that controls the connection between the first inspection line and the first pixel group and a second switching part that controls the connection between the second inspection line and the second pixel group and a dummy circuit including a dummy transistor that is electrically connected to the switching part and including a first dummy electrode, a second dummy electrode that is connected to the first dummy electrode, and a dummy control electrode.

20 Claims, 8 Drawing Sheets

DISPLAY DEVICE

CROSS-REFERENCE TO RELATED APPLICATION

This U.S. non-provisional patent application claims priority under 35 U.S.C. § 119 of Korean Patent Application No. 10-2018-0015829, filed on Feb. 8, 2018, the disclosure of which is hereby incorporated by reference in its entirety.

BACKGROUND

1. Field of Disclosure

The present disclosure relates to a display device. More particularly, the present disclosure relates to a display device capable of inspecting a crack.

2. Description of the Related Art

A display panel including a flexible substrate may be partially curved or bent. For example, a portion of a non-display area in which no image is displayed is bent to implement a narrow bezel. In addition, a portion of a display area in which an image is displayed may be bent to realize a display device having a curvature. In this case, when a crack occurs through signal lines arranged in the flexible substrate, the driving of the display device becomes poor, and a quality of the display device is deteriorated.

SUMMARY

The present disclosure provides a display device having improved reliability and capable of inspecting a crack of a display panel and protecting an inspection circuit from static electricity.

An embodiments of the inventive concept provides a display device including a display panel including a display area, a non-display area disposed around the display area, and a plurality of pixels disposed in the display area, a first inspection line disposed in the non-display area and electrically connected to a first pixel group among the plurality of pixels, a second inspection line passing through a portion of the non-display area and electrically connected to a second pixel group that is different from the first pixel group among the plurality of pixels, and an inspection circuit disposed in the non-display area and connecting the first inspection line to the first pixel group and connecting the second inspection line to the second pixel group. The inspection circuit includes a switching part including a first switching part that controls a connection between the first inspection line and the first pixel group and a second switching part that controls a connection between the second inspection line and the second pixel group and a dummy circuit including a dummy transistor electrically that is connected to the switching part and including a first dummy electrode, a second dummy electrode that is connected to the first dummy electrode, and a dummy control electrode.

The dummy circuit may include a first dummy circuit connected between the first switching part and the first inspection line and a second dummy circuit connected between the second switching part and the second inspection line.

The dummy circuit may be connected between the first switching part and the first inspection line or between the second switching part and the second inspection line.

Each of the first switching part and the second switching part may include a switching transistor, the switching transistor may include a switching control electrode, a first switching electrode that is connected to the first inspection line or the second inspection line, and a second switching electrode that is connected to the first pixel group or the second pixel group. The dummy control electrode and the switching control electrode may receive a same signal, and the first dummy electrode and the second dummy electrode may be connected to the first inspection line or the second inspection line.

The plurality of pixels may include a first pixel displaying a first color, a second pixel displaying a second color that is different from the first color, and a third pixel displaying a third color that is different from the first color and the second color. The first pixel group may include at least one pixel among the first, second, and third pixels, and the second pixel group may include pixels displaying the same color as the first pixel group.

Each of the first pixel group and the second pixel group may be provided in a plural number, the first inspection line may be electrically connected to the first pixel groups, and the second inspection line may be electrically connected to the second pixel groups.

The display device may further include an inspection voltage pad to apply an inspection voltage to each of the first inspection line and the second inspection line, the first inspection line may be electrically connected to the inspection voltage pad and the first switching part, and the second inspection line may be electrically connected to the inspection voltage pad and the second switching part.

The second inspection line may include a first sub-inspection line extending from the inspection voltage pad and passing through a portion of the non-display area and a second sub-inspection line extending from the first sub-inspection line and connected to the second switching part.

The first inspection line may include a matching resistor reducing a difference between a first voltage that is applied to the first pixel group through the first inspection line and a second voltage that is applied to the second pixel group through the second inspection line.

The matching resistor may be provided between the inspection voltage pad and the first switching part.

The display device may further include a plurality of pads arranged in the non-display area and receiving a data voltage applied to the plurality of pixels, and the inspection circuit may be disposed between the display area and the pads when viewed in a plan view.

Another embodiment of the inventive concept provides a display device including a display panel including a display area, a non-display area surrounding the display area, and a plurality of pixels disposed in the display area, an inspection line electrically connected to one or more pixels among the plurality of pixels, a switching transistor disposed in the non-display area to control a connection between the inspection line and the one or more pixels among the plurality of pixels, and a dummy transistor disposed in the non-display area and connected to the inspection line. The switching transistor includes a switching control electrode, a first switching electrode that is electrically connected to the inspection line, and a second switching electrode that is electrically connected to the one or more pixels among the plurality of pixels. The dummy transistor includes a dummy control electrode receiving a same signal as the switching control electrode, a first dummy electrode that is electrically connected to the inspection line, and a second dummy electrode that is electrically connected to the inspection line.

The inspection line may be provided in a plural number. The inspection lines may include a first inspection line electrically connected to a first pixel group among the plurality of pixels and a second inspection line electrically connected to a second pixel group among the plurality of pixels after passing through a portion of the non-display area, and the first pixel group and the second pixel group may display a same color.

The first dummy electrode and the second dummy electrode may be connected to each other.

Another embodiment of the inventive concept provides a display device including a display panel including a display area, a non-display area surrounding the display area, a plurality of first pixel groups each including a plurality of pixels arranged in a first direction and being arranged in a second direction that crosses the first direction, and a plurality of second pixel groups each including a plurality of pixels arranged in the first direction and being arranged in the second direction, a first inspection line electrically connected to the first pixel groups, a second inspection line electrically connected to the second pixel groups after passing through a portion of the non-display area, and an inspection circuit disposed in the non-display area to connect the first inspection line to the first pixel groups and to connect the second inspection line to the second pixel groups. The inspection circuit includes a switching part including a first switching part that controls a connection between the first inspection line to the plurality of first pixel groups and a second switching part that controls a connection between the second inspection line to the plurality of second pixel groups and a dummy circuit electrically connected to the switching part.

The dummy circuit may include a first dummy circuit connected between the first switching part and the first inspection line and a second dummy circuit connected between the second switching part and the second inspection line.

The display device may further include an inspection pad part to apply an inspection voltage to the first inspection line and the second inspection line. The first inspection line may further include a matching resistor, and the matching resistor may be provided between a part receiving the inspection voltage and the first dummy circuit.

The dummy circuit may include a dummy transistor, and the dummy transistor may include a dummy control electrode receiving a same signal as a signal used to control the first switching part and the second switching part, a first dummy electrode connected to the first inspection line or the second inspection line, and a second dummy electrode connected to the first dummy electrode.

The plurality of first pixel groups may be alternately arranged with the plurality of second pixel groups.

The plurality of first pixel groups and the plurality of second pixel groups may display a same color.

According to the above, the dummy circuit is provided to protect the switching part from the static electricity. Accordingly, the switching transistor of the switching part may be prevented from being damaged due to the static electricity.

In addition, the plural pixel groups are connected to one of the inspection lines. When the crack inspection is performed on the display panel, the pixel groups in which a crack occurs emit a light of a predetermined color. Accordingly, it is easy to determine whether the crack has occurred based on the emitted light during the crack inspection.

BRIEF DESCRIPTION OF THE DRAWINGS

The above and other advantages of the present disclosure will become readily apparent by reference to the following detailed description when considered in conjunction with the accompanying drawings wherein.

DETAILED DESCRIPTION

Figure 1:
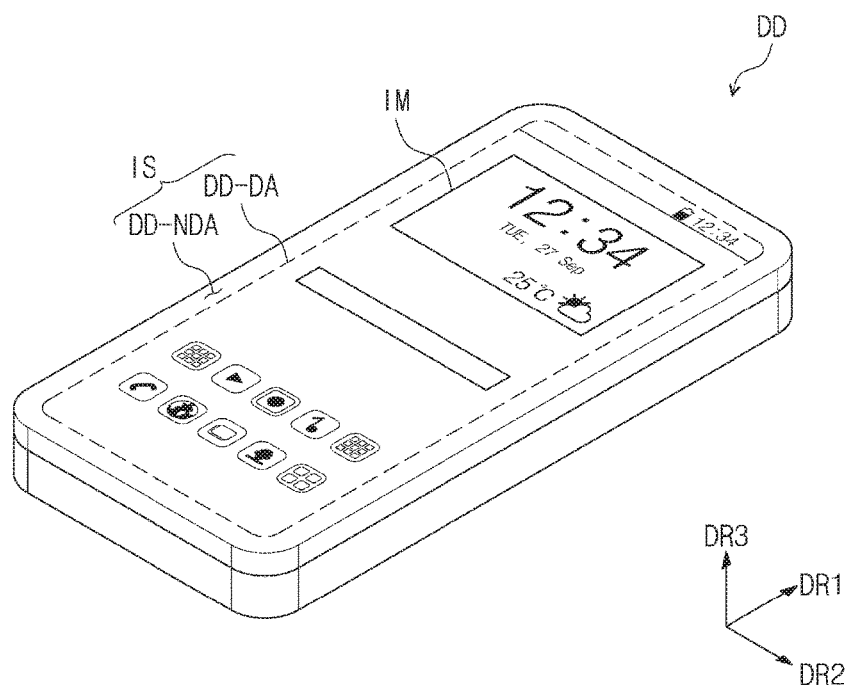
FIG. 1 is a perspective view showing a display device according to an exemplary embodiment of the present disclosure.

Hereinafter, the present disclosure will be explained in detail with reference to the accompanying drawings. It will be understood that when an element or layer is referred to as being "on", "connected to" or "coupled to" another element or layer, it can be directly on, connected or coupled to the other element or layer or one or more intervening elements or layers may be present.

Like numbers refer to like elements throughout the present disclosure. In the drawings, the thickness, ratio, and size of components are exaggerated for clarity. As used herein, the term "and/or" includes any and all combinations of one or more of the associated listed items.

The use of the terms first, second, etc. does not denote any order or importance, but rather the terms first, second, etc. are used to distinguish one element from another. Thus, a first element, component, region, layer, or section discussed below could be termed a second element, component, region, layer, or section without departing from the teachings of the present disclosure. It is to be understood that the singular forms "a," "an," and "the" include plural referents unless the context clearly dictates otherwise.

It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

FIG. 1 is a perspective view showing a display device DD according to an exemplary embodiment of the present disclosure.

Referring to FIG. 1, the display device DD displays an image IM through a display surface IS. In FIG. 1, the display surface IS is shown to be parallel to a surface defined by a first direction DR1 and a second direction DR2 that crosses the first direction DR1, however, according to another embodiment, a display surface (not shown) of a display device (not shown) may have a curved shape.

A third direction DR3 indicates a normal line direction of the display surface IS, i.e., a thickness direction of the display device DD. Front (or upper) and rear (or lower) surfaces of the display device DD are distinguished from each other by the third direction DR3. However, directions indicated by the first, second, and third directions DR1, DR2, and DR3 are relative to each other, and thus the directions indicated by the first, second, and third directions DR1, DR2, and DR3 may be changed to other directions.

FIG. 1 shows a mobile electronic device as the display device DD. However, the display device may be applied to a large-sized electronic device, such as a television set, a monitor, an outdoor billboard, etc., and a small and medium-sized electronic device, such as a personal computer, a notebook computer, a personal digital assistant, a car navigation unit, a game unit, a smartphone, a tablet computer, a camera, etc. However, these are merely suggested electronic devices, and the display device DD may be applied to various other electronic devices without departing from the concept of the present disclosure.

The display surface IS includes a display area DD-DA in which the image IM is displayed and a non-display area DD-NDA that is disposed adjacent to the display area DD-DA. The image IM is not displayed through the non-display area DD-NDA. FIG. 1 shows application icons as the image IM. For example, the display area DD-DA may have a quadrangular shape. The non-display area DD-NDA may surround the display area DD-DA, but it should not be limited thereto or thereby. The display area DD-DA and the non-display area DD-NDA may be designed relative to each other. In addition, the non-display area DD-NDA may not be provided to the front surface of the display device DD.

Figure 2A:
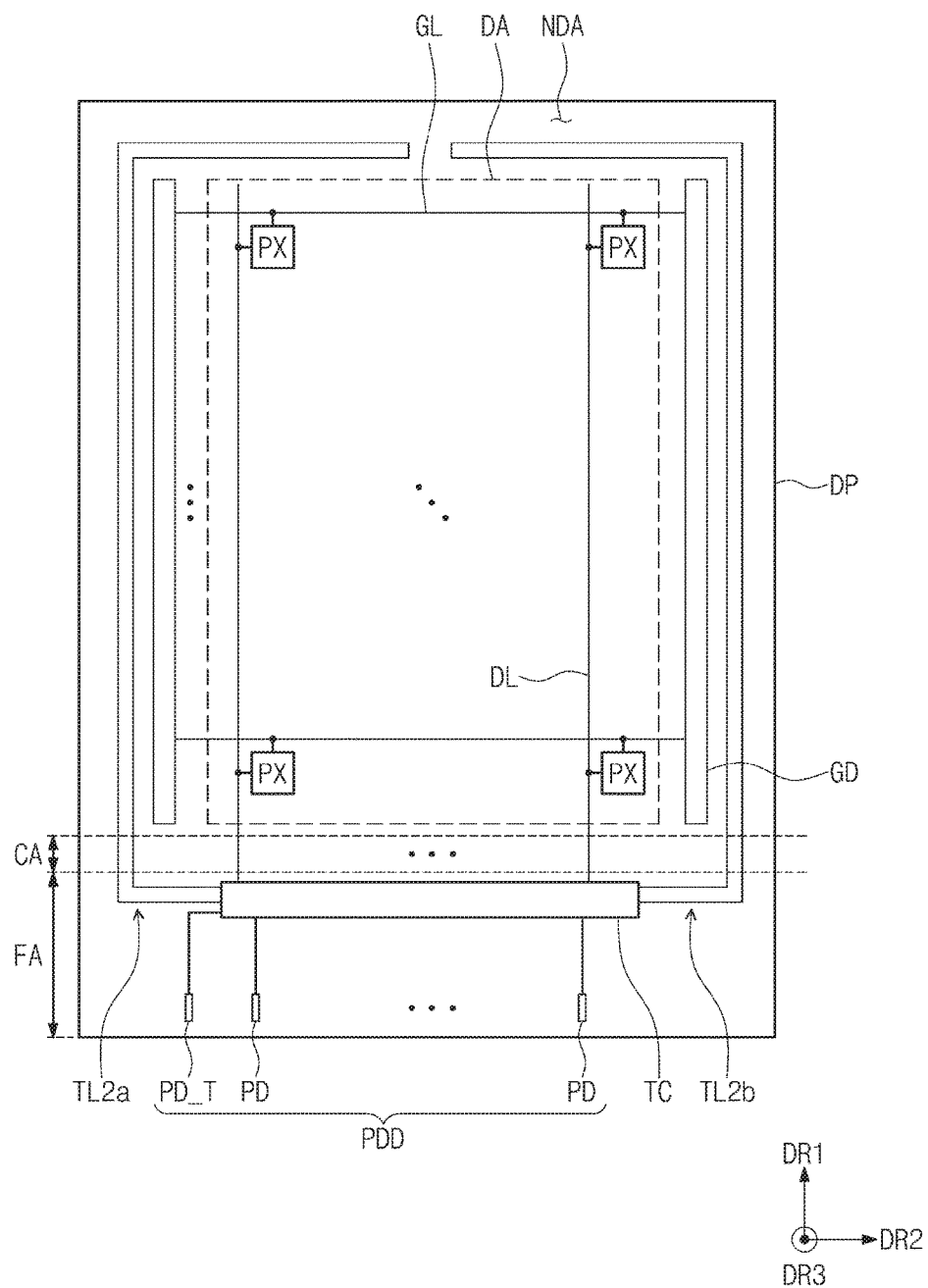
FIG. 2A is a plan view showing a display panel according to an exemplary embodiment of the present disclosure.
Figure 2B:
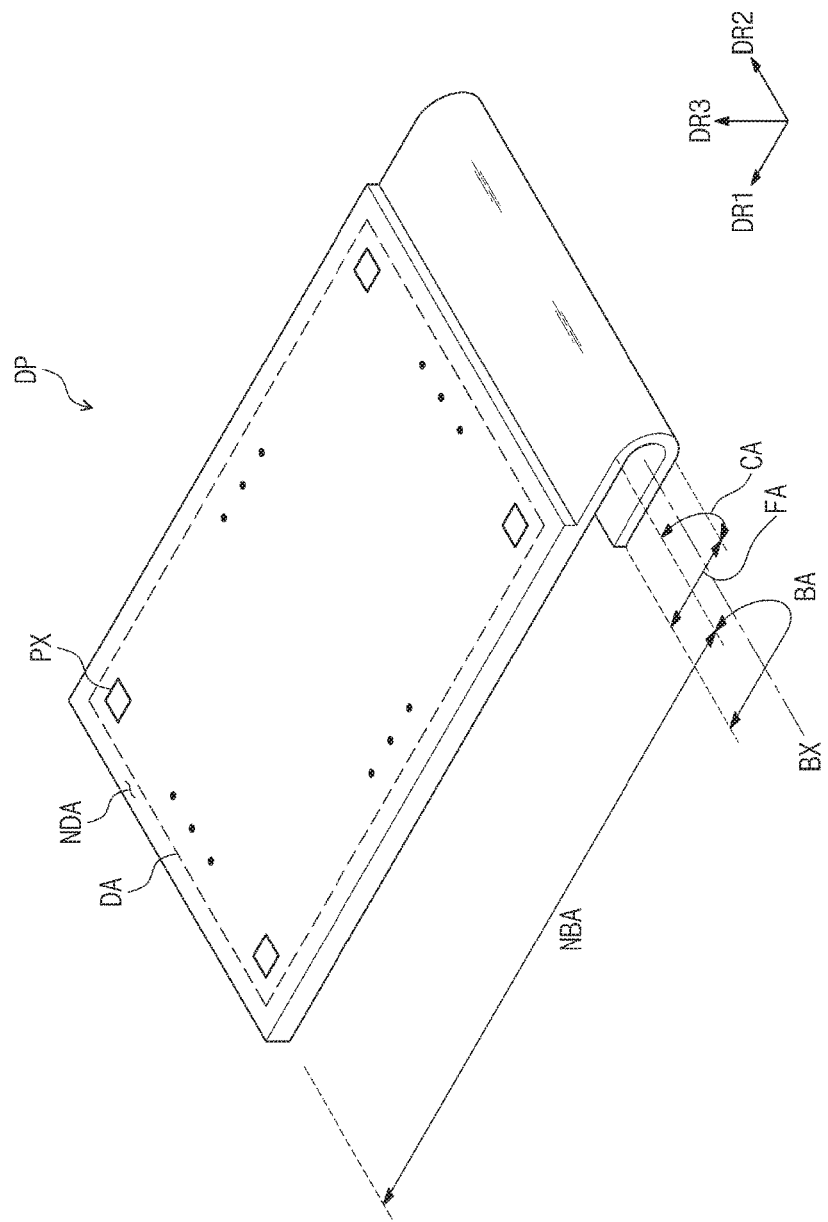
FIG. 2B is a perspective view showing a display panel according to an exemplary embodiment of the present disclosure.

FIG. 2A is a plan view showing a display panel DP according to an exemplary embodiment of the present disclosure, and FIG. 2B is a perspective view showing the display panel DP according to an exemplary embodiment of the present disclosure.

Referring to FIGS. 2A and 2B, the display panel DP may include a display area DA and a non-display area NDA. The display area DA is an area in which an image is displayed, and the non-display area NDA is an area in which the image is not displayed. The non-display area NDA may be disposed around the display area DA.

The display area DA of the display panel DP corresponds to the display area DD-DA (refer to FIG. 1) of the display device DD (refer to FIG. 1), and the non-display area NDA corresponds to the non-display area DD-NDA (refer to FIG. 1) of the display device DD (refer to FIG. 1), however, they should not be limited thereto or thereby. That is, the display areas DA and DD-DA and the non-display areas NDA and DD-NDA may be changed depending on structure and design of the display panel DP.

The display panel DP may include a substrate such as a silicon substrate, a plastic substrate, an insulating film, or a structure of plural insulating layers. The substrate of the display panel DP may have a flexibility, and at least a portion of the display panel DP may be bent. FIG. 2B shows a bending state in which at least a portion of the display panel DP is bent.

Referring to FIG. 2B, the display panel DP is divided into a first area NBA (hereinafter, referred to as a "non-bending area") and a second area BA (hereinafter, referred to as a "bending area) with respect to the bending portion of the display panel DP. The bending area BA includes a curvature area CA that has a predetermined curvature in the bending state and a facing area FA that faces the non-bending area NBA in the bending state. The non-bending area NBA, the curvature area CA, and the facing area FA are arranged along the first direction DR1. The bending area BA is bent along a bending axis BX extending in the second direction DR2, the curvature area CA of the bending area BA is curved along the bending axis BX, and the facing area FA is disposed to face a portion of the non-bending area NBA in the third direction DR3.

A plurality of pixels PX and gate lines GL and data lines DL that are electrically connected to the pixels PX may be arranged in the display area DA. One or more gate drivers GD, an inspection circuit TC, a pad part PDD, and inspection lines TL2a and TL2b may be arranged in the non-display area NDA.

Each of the gate lines GL and each of the data lines DL may be electrically connected to a corresponding pixel among the pixels PX. The inspection circuit TC may be electrically connected to one or more data lines DL among the data lines DL.

The inspection lines TL2a and TL2b may be electrically connected to the inspection circuit TC after passing through a portion of the non-display area NDA. This will be described in detail with reference to FIG. 3A.

In FIG. 2A, two gate drivers GD are arranged in areas facing each other such that the display area DA is disposed between the areas, i.e., the two gate drivers GD are disposed at both sides of the display area DA. The gate drivers GD apply gate signals to both ends of each of the gate lines GL to prevent a charging failure that may be caused by a delay of the gate signals. However, according to other embodiments, one of the gate drivers GD may be omitted, and thus the gate driver may be disposed only at one side of the display area DA.

The pad part PDD includes an inspection voltage pad PD_T and a plurality of pads PD. The inspection voltage pad PD_T is electrically connected to the inspection circuit TC to transmit an inspection voltage that is provided from an external source (not shown) to the inspection circuit TC. The pads PD are electrically connected to the data lines DL in a one-to-one correspondence. Although not shown in figures, the display panel DP may further include a data driving circuit that is coupled to the pad part PDD in a chip-on-film form, however, it should not be limited thereto or thereby. According to other embodiments, the data driving circuit may be directly integrated to the display panel DP. The data driving circuit may be electrically connected to the data lines DL and transmit data voltages to the data lines DL.

The display area DA may be provided to overlap the non-bending area NBA, and the inspection circuit TC and the pad part PDD may be arranged in the facing area FA. The curvature area CA may correspond to an area between the display area DA and an area on which the inspection circuit TC is mounted. That is, the inspection circuit TC is disposed in the facing area FA and is disposed under the non-bending area NBA in the bending state. The area in which the inspection circuit TC is disposed may be secured by adjusting an area of the facing area FA. Accordingly, the area in which the inspection circuit TC is disposed may be more easily secured.

Figure 3A:
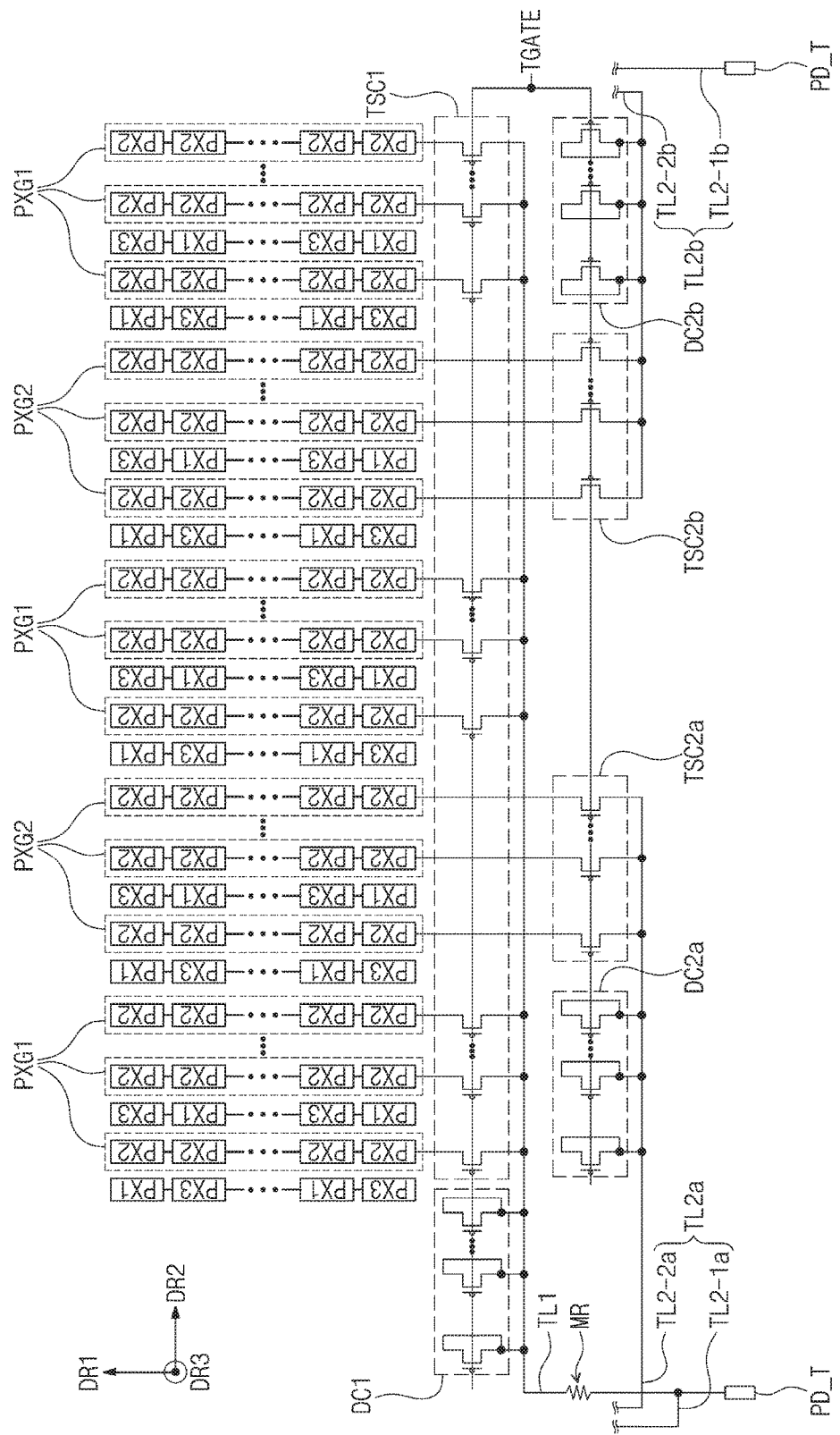
FIG. 3A is a plan view showing a display panel and an inspection circuit according to an exemplary embodiment of the present disclosure.
Figure 3B:
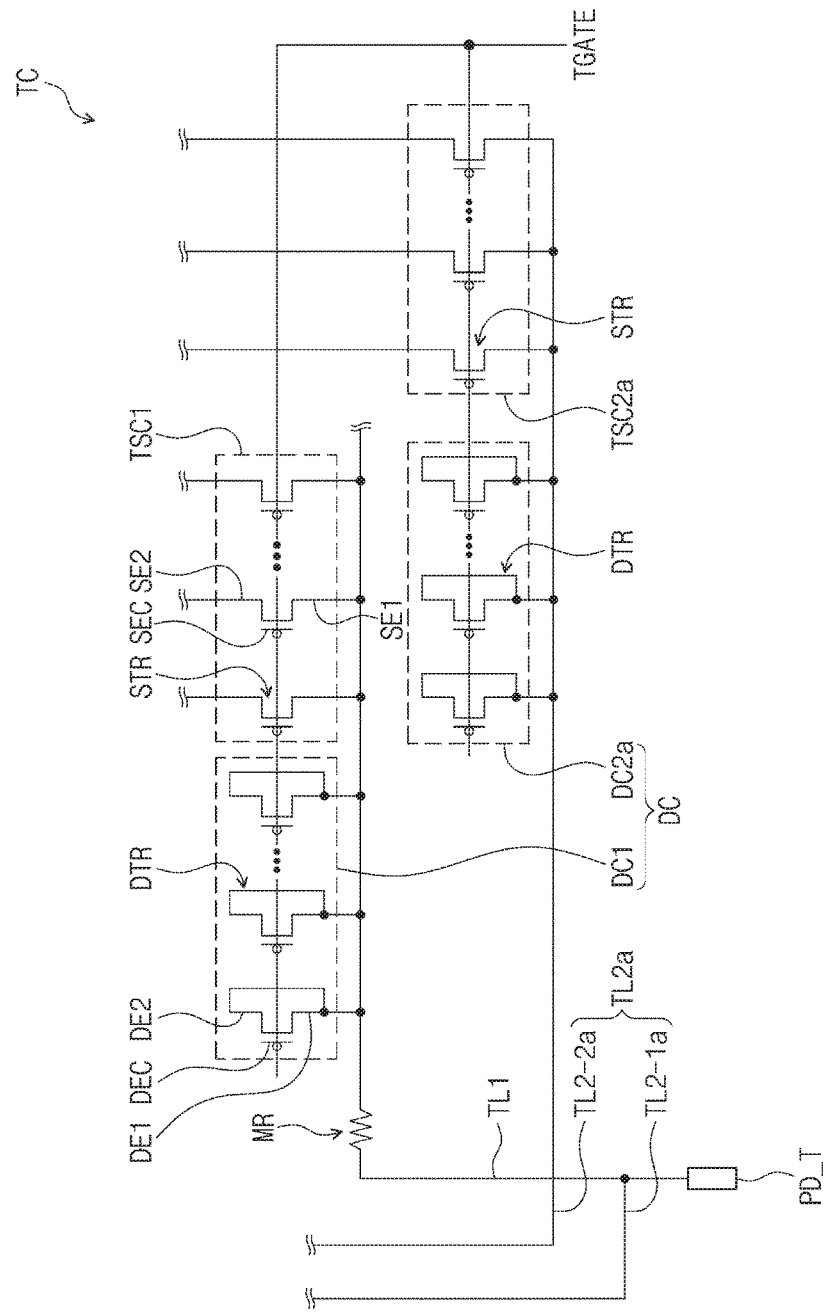
FIG. 3B is a circuit diagram showing a portion of an inspection circuit.

FIG. 3A is a plan view showing the display panel DP and the inspection circuit TC according to an exemplary embodiment of the present disclosure, and FIG. 3B is a circuit diagram showing a portion of the inspection circuit TC.

Referring to FIGS. 3A and 3B, the inspection line receiving the inspection voltage from the inspection voltage pad PD_T may include a first inspection line TL1 and second inspection lines TL2a and TL2b.

The first inspection line TL1 may include a matching resistor MR, and the second inspection lines TL2a and TL2b may pass through the non-display area NDA (refer to FIG. 2A).

The second inspection lines TL2a and TL2b surround a portion of the display area DA when viewed in a plan view, and each of the second inspection lines TL2a and TL2b has a loop shape. In the present exemplary embodiment, two second inspection lines TL2a and TL2b will be described as a representative example, but the number of the second inspection lines should not be limited to two. For instance, according to other embodiments, only one second inspection line TL2a may be provided, or three or more second inspection lines may be provided.

The second inspection line TL2a includes a first sub-inspection line TL2-1a and a second sub-inspection line TL2-2a. The second inspection line TL2b includes a first sub-inspection line TL2-1b and a second sub-inspection line TL2-2b. The first sub-inspection lines TL2-1a and TL2-1b extend from the inspection voltage pad PD_T and pass through a portion of the non-display area NDA (refer to FIG. 2A), and the second sub-inspection lines TL2-2a and TL2-2b extend from the first sub-inspection lines TL2-1a and TL2-1b and are connected to the inspection circuit TC.

The pixels PX (refer to FIG. 2A) may include a first pixel PX1, a second pixel PX2, and a third pixel PX3. For example, the first pixel PX1 may display a first color, the second pixel PX2 may display a second color that is different from the first color, and the third pixel PX3 may display a third color that is different from the first and second colors.

In the present exemplary embodiment, the firs pixel PX1 may display a red color, the second pixel PX2 may display a green color, and the third pixel PX3 may display a blue color, however, the colors displayed by the first, second, and third pixels PX1, PX2, and PX3 should not be limited thereto or thereby. For example, according to other embodiments, the pixels PX may further include a fourth pixel displaying a white color or a mixed color.

The first pixel PX1 and the third pixel PX3 may be alternately arranged with each other along the first direction DR1. The second pixel PX2 may be provided in a plural number and arranged along the first direction DR1. A column in which the first pixel PX1 and the third pixel PX3 are alternately arranged with each other and a column in which the second pixels PX2 are arranged may be alternately arranged with each other along the second direction DR2. This structure may be referred to as a "pentile structure".

The first inspection line TL1 is electrically connected to a first pixel group PXG1 among the pixels PX (refer to FIG. 2A), and the second inspection lines TL2a and TL2b are electrically connected to a second pixel group PXG2 among the pixels PX (refer to FIG. 2A).

Each of the first pixel group PXG1 and the second pixel group PXG2 may include one or more pixels. The pixels included in the first pixel group PXG1 and the second pixel group PXG2 may display the same color.

As shown in FIG. 3A, each of the first pixel group PXG1 and the second pixel group PXG2 includes the second pixel PX2, but they should not be limited thereto or thereby. That is, according to other embodiments, each of the first pixel group PXG1 and the second pixel group PXG2 may include the first pixel PX1 and the third pixel PX3.

Each of the first pixel group PXG1 and the second pixel group PXG2 may be provided in a plural number. The first pixel groups PXG1 may be electrically connected to the first inspection line TL1, and the second pixel groups PXG2 may be electrically connected to the second inspection lines TL2a and TL2b. The first pixel groups PXG1 may be alternately arranged with the second pixel groups PXG2 in the second direction DR2.

In FIG. 3A, the first pixel groups PXG1 that is electrically connected to the first inspection line TL1, the second pixel groups PXG2 that is electrically connected to the second inspection line TL2a, the first pixel groups PXG1 that is electrically connected to the first inspection line TL1, the second pixel groups PXG2 that is electrically connected to the second inspection line TL2b, and the first pixel groups PXG1 that is electrically connected to the first inspection line TL1 are sequentially arranged in the second direction DR2.

The inspection circuit TC may control a connection between the first inspection line TL1 and the first pixel groups PXG1 and a connection between the second inspection lines TL2a and TL2b and the second pixel groups PXG2.

The inspection circuit TC may include a first switching part TSC1, second switching parts TSC2a and TSC2b, and a dummy circuit DC.

The first switching part TSC1 may control the connection between the first inspection line TL1 and the first pixel groups PXG1. The second switching part TSC2a may control the connection between the second inspection line TL2a and the second pixel groups PXG2. The second switching part TSC2b may control the connection between the second inspection line TL2b and the second pixel groups PXG2.

Each of the first switching part TSC1, and the second switching parts TSC2a and TSC2b may include a switching transistor STR. The switching transistor STR may be provided in a plural number. The switching transistor STR may electrically connect the data line DL (refer to FIG. 2A) to the first inspection line TL1 or the second inspection lines TL2a and TL2b.

The switching transistor STR may include a switching control electrode SEC, a first switching electrode SE1, and a second switching electrode SE2.

The switching control electrode SEC may receive a switching control signal TGATE. The switching control signal TGATE may control an on/off of the switching transistor STR. When a crack inspection is performed on the display panel DP (refer to FIG. 2A), the switching transistor STR may be turned on in response to the switching control signal TGATE. The first switching electrode SE1 may be electrically connected to one of the inspection lines, TL1, TL2a, and TL2b. For example, the first switching electrode SE1 of the first switching part TSC1 may be connected to the first inspection line TL1, the first switching electrode SE1 of the second switching part TSC2a may be connected to the second inspection line TL2a, and the first switching electrode SE1 of the second switching part TSC2b may be connected to the second inspection line TL2b.

The second switching electrode SE2 may be connected to the data line DL (refer to FIG. 2A). For example, the second switching electrode SE2 of the first switching part TSC 1 may be connected to the data line that is connected to the first pixel group PXG1, and the second switching electrode SE2 of the second switching parts TSC2a and TSC2b may be connected to the data line that is connected to the second pixel group PXG2.

According to the crack inspection on the display panel DP (refer to FIG. 2A), the first pixel groups PXG1 and the second pixel groups PXG2 may emit a light during a first period of the crack inspection. For example, the first pixel groups PXG1 and the second pixel groups PXG2 emit the light with a maximum brightness during the first period. After the first period, the inspection voltage is applied to the first pixel groups PXG1 and the second pixel groups PXG2 respectively through the first inspection line TL1 and the second inspection lines TL2a and TL2b during a second period of the crack inspection. The inspection voltage may be a voltage corresponding to a black data signal.

When a crack occurs in the display panel DP (refer to FIG. 2A), a resistance of the second inspection lines TL2a and/or TL2b may increase. Accordingly, the pixels of the second pixel groups PXG2 that receive the voltage through the second inspection lines TL2a and TL2b during the second period may not be charged to a voltage level corresponding to the black data signal. Therefore, when a crack occurs, the pixels of the second pixel groups PXG2 may emit a light other than a light corresponding to the black data signal. This may be used to determine whether the crack has occurred.

Since the second inspection lines TL2a and TL2b that pass through the non-display area NDA (refer to FIG. 2A) of the display panel DP (refer to FIG. 2A) are longer than the first inspection line TL1, the second inspection lines TL2a and TL2b have a line resistance greater than a line resistance of the first inspection line TL1. Accordingly, in order to compensate for a difference between the line resistances, the matching resistor MR may be provided to the first inspection line TL1. The matching resistor MR may be provided between the inspection voltage pad PD_T and the first switching part TSC1.

The matching resistor MR may reduce a difference between a first voltage that is applied to the first pixel group PXG1 through the first inspection line TL1 and a second voltage that is applied to the second pixel group PXG2 through the second inspection lines TL2a and TL2b in a normal state (e.g., a state in which no crack occurs). When the resistance of the second inspection lines TL2a and TL2b increases due to a crack (i.e., an abnormal state), the second voltage may be lower than the first voltage. That is, the difference between the first voltage and the second voltage may increase due to the crack.

When a crack occurs, the plural second pixel groups PXG2 that are connected to the second inspection line TL2a or TL2b emit a light during the second period of the crack inspection. Accordingly, it is easy to determine whether the crack has occurred depending on the light emitted by the plural second pixel groups PXG2.

When static electricity flows through the first switching part TSC1 and the second switching part TSC2, the switching transistor STR of the first and second switching parts TSC1 and TSC2 may be damaged. The dummy circuit DC may be provided to prevent the switching transistor STR from being damaged. The dummy circuit DC may protect the first switching part TSC1 and the second switching part TSC2 from the static electricity.

The dummy circuit DC may include a first dummy circuit DC1 and second dummy circuits DC2a and DC2b. The first dummy circuit DC1 may be electrically connected between the first inspection line TL1 and the first switching part TSC1. The second dummy circuit DC2a may be electrically connected between the second inspection line TL2a and the second switching part TSC2a. The second dummy circuit DC2b may be electrically connected between the second inspection line TL2b and the second switching part TSC2b.

The dummy circuit DC may be connected to the first inspection line TL1 and the second inspection lines TL2a and TL2b and may extend to the first switching part TSC1 and the second switching part TSC2 of the inspection circuit TC. Accordingly, when the static electricity enters the inspection circuit TC, the static electricity may first enter the dummy circuit DC before entering the first switching part TSC1 and the second switching part TSC2.

For example, the static electricity flowing through the first inspection line TL1 may enter the first dummy circuit DC1. The static electricity may damage dummy transistors DTR included in the first dummy circuit DC1. The static electricity passing through the first dummy circuit DC1 may become weak, thereby reducing a probability that the static electricity damages the first switching part TSC1. Similarly, the static electricity flowing through the second inspection line TL2a may enter the second dummy circuit DC2a. The static electricity may damage dummy transistors DTR included in the second dummy circuit DC2a, thereby reducing a probability that the static electricity damages the second switching part TSC2a.

The dummy circuit DC may include the dummy transistors DTR. The dummy transistors DTR may be formed by the same process as the switching transistor STR. Each of the dummy transistors DTR may include a dummy control electrode DEC, a first dummy electrode DE1, and a second dummy electrode DE2.

The first dummy electrode DE1 may be electrically connected to one of the inspection lines. For example, the first dummy electrode DE1 of the first dummy circuit DC1 may be connected to the first inspection line TL1, the first dummy electrode DE1 of the second dummy circuit DC2a may be connected to the second inspection line TL2a, and the first dummy electrode DE1 of the second dummy circuit DC2b may be connected to the second inspection line TL2b.

The second dummy electrode DE2 may be connected to the first dummy electrode DE1. That is, the second dummy electrode DE2 of the first dummy circuit DC1 may be connected to the first inspection line TL1, the second dummy electrode DE2 of the second dummy circuit DC2a may be connected to the second inspection line TL2a, and the second dummy electrode DE2 of the second dummy circuit DC2b may be connected to the second inspection line TL2b.

The dummy control electrode DEC may receive the same signal as the switching control electrode SEC. That is, the dummy control electrode DEC may receive the switching control signal TGATE. Accordingly, when the switching transistor STR is turned on during the crack inspection, the dummy transistors DTR may be turned on as well. When an abnormal voltage having the voltage level that is lower than that of the static electricity but equal to or greater than a voltage level that is sufficient enough to change characteristics of the switching transistor STR enters, the abnormal voltage may be suppressed by the turned-on dummy transistors DTR. Accordingly, the dummy transistors DTR can suppress a change of the characteristics of the switching transistor STR during the crack inspection even when an abnormal voltage enters through the switching control signal TGATE. Thus, reliability of the crack inspection may be improved.

In the present exemplary embodiment of the present disclosure, the number of the dummy transistors DTR included in the first dummy circuit DC1 may be equal to the number of the dummy transistors DTR included in the second dummy circuit DC2a or DC2b, but they should not be limited thereto or thereby. For example, according to other embodiments, the number of the dummy transistors DTR included in the first dummy circuit DC1 may be different from the number of the dummy transistors DTR included in the second dummy circuit DC2a or DC2b. For example, the number of the dummy transistors DTR included in the first dummy circuit DC1 may be different from the number of the dummy transistors DTR included in the second dummy circuit DC2a when there is a difference between available spaces for the dummy transistors DTR in the first dummy circuit DC1 and the second dummy circuit DC2a or DC2b depending on the line design. In addition, when a probability that the static electricity is generated in the second inspection line TL2a or TL2b that is connected to the second dummy circuit DC2a is higher than a probability that the static electricity is generated in the first inspection line TL1 that is connected to the first dummy circuit DC1 or an intensity of the static electricity that is generated in the second inspection line TL2a or TL2b is greater than an intensity of the static electricity that is generated in the first inspection line TL1, the number of the dummy transistors DTR included in the second dummy circuit DC2a or DC2b may be greater than the number of the dummy transistors DTR included in the first dummy circuit DC1.

Figure 4:
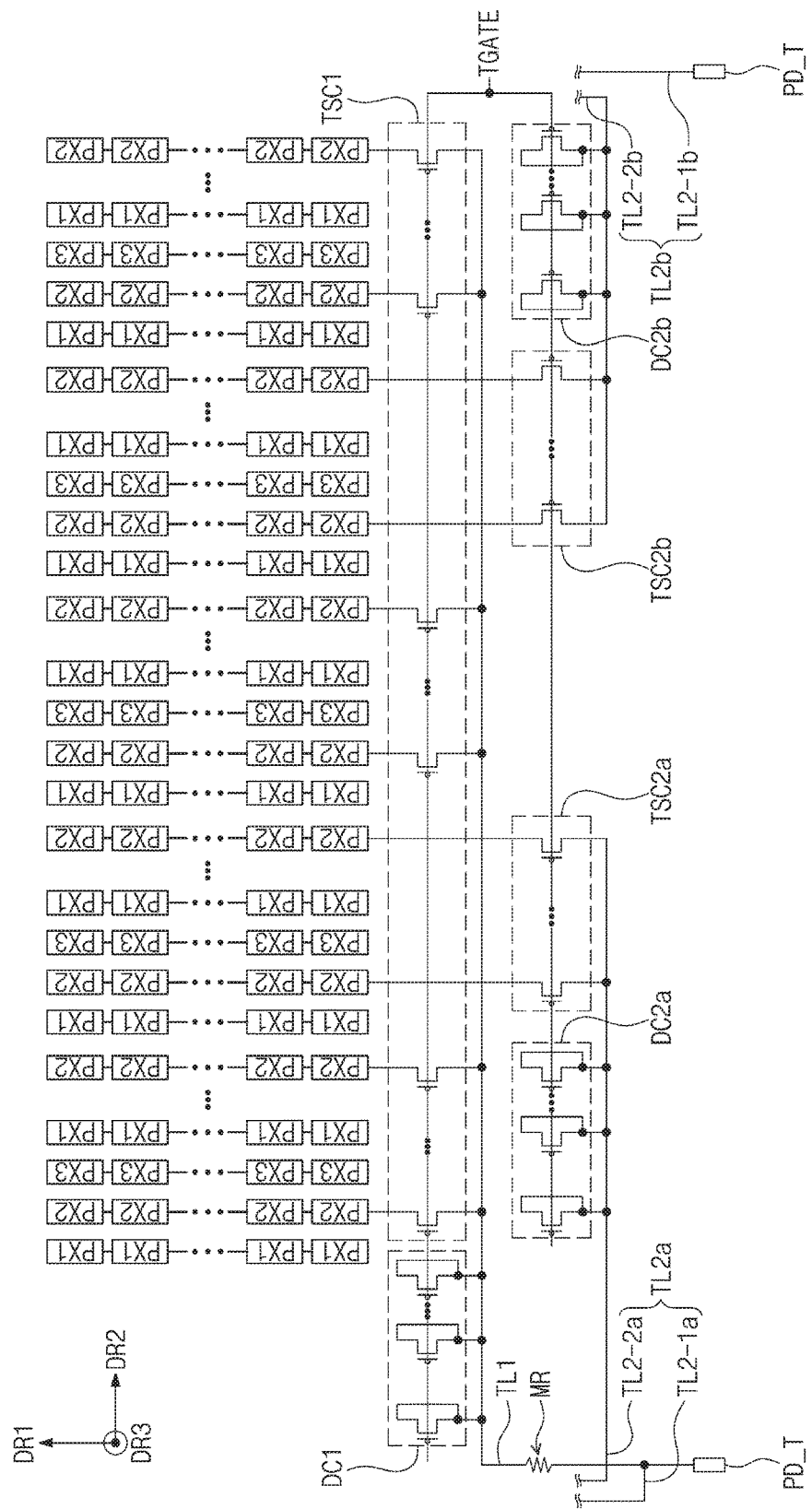
FIG. 4 is a plan view showing a display panel and an inspection circuit according to an exemplary embodiment of the present disclosure.

FIG. 4 is a plan view showing a display panel and an inspection circuit according to an exemplary embodiment of the present disclosure. In FIG. 4, the same reference numerals denote the same elements in FIG. 3A, and thus detailed descriptions of the same elements will be omitted.

Referring to FIG. 4, the pixels PX (refer to FIG. 2A) may include the first pixel PX1, the second pixel PX2, and the third pixel PX3. The first pixel PX1, the second pixel PX2, and the third pixel PX3 are alternately arranged with each other in the second direction DR2. The first pixel PX1 is provided in a plural number, and the first pixels PX1 are arranged in the first direction DR1. The second pixel PX2 is provided in a plural number, and the second pixels PX2 are arranged in the first direction DR1. The third pixel PX3 is provided in a plural number, and the third pixels PX3 are arranged in the first direction DR1.

In the present exemplary embodiment, the first pixel PX1 may display the red color, the second pixel PX2 may display the green color, and the third pixel PX3 may display the blue color.

The first inspection line TL1 and the second inspection lines TL2a and TL2b may be connected to the second pixel PX2. The green color displayed by the second pixel PX2 has a visibility higher than that of other colors in a dark (e.g., black) background. When a crack has occurred, the second pixel PX2 that is connected to the second inspection lines TL2a and TL2b fails to charge to the voltage level corresponding to the black data signal during the crack inspection, and thus the second pixel PX2 emits a light of the green color. Accordingly, it is easy to determine occurrence of a crack even though the second pixel PX2 emits a weak light of the green color.

Figure 5:
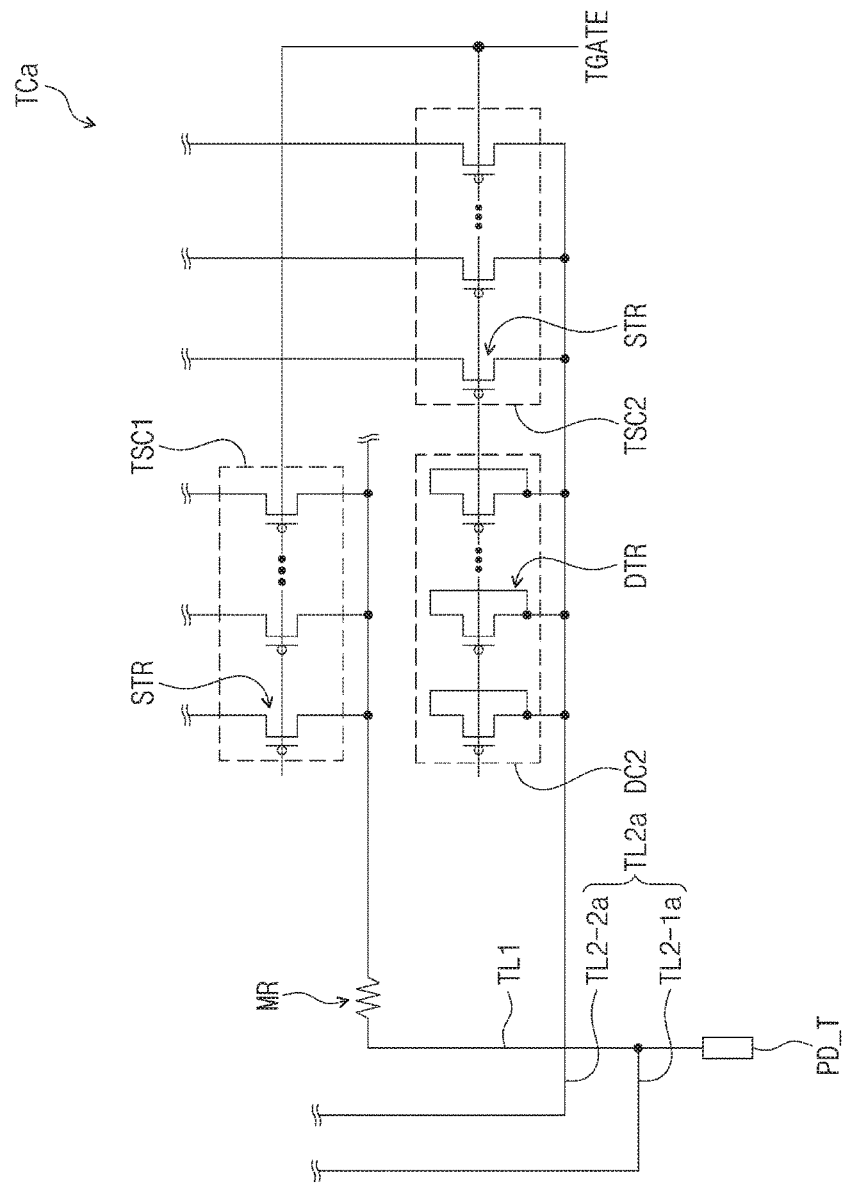
FIG. 5 is an equivalent circuit diagram showing an inspection circuit according to another exemplary embodiment of the present disclosure.

FIG. 5 is an equivalent circuit diagram showing an inspection circuit TCa according to another exemplary embodiment of the present disclosure.

When compared with FIGS. 3A and 3B, the first dummy circuit DC1 (refer to FIG. 3B) may be omitted from the inspection circuit TCa shown in FIG. 5.

The second inspection line TL2a may have a loop shape passing through a portion of the non-display area NDA (refer to FIG. 2A) of the display panel DP (refer to FIG. 2A). Accordingly, the second inspection line TL2a may be vulnerable to the static electricity. Thus, the inspection circuit TCa may have only the second dummy circuit DC2 that is connected to the second inspection line TL2a.

The second dummy circuit DC2 may be connected to the second inspection line TL2a. Accordingly, the static electricity flowing through the second inspection line TL2a may enter the second dummy circuit DC2 before entering the second switching part TSC2, thereby preventing a damage to the second switching part TSC2 due to the static electricity.

Figure 6:
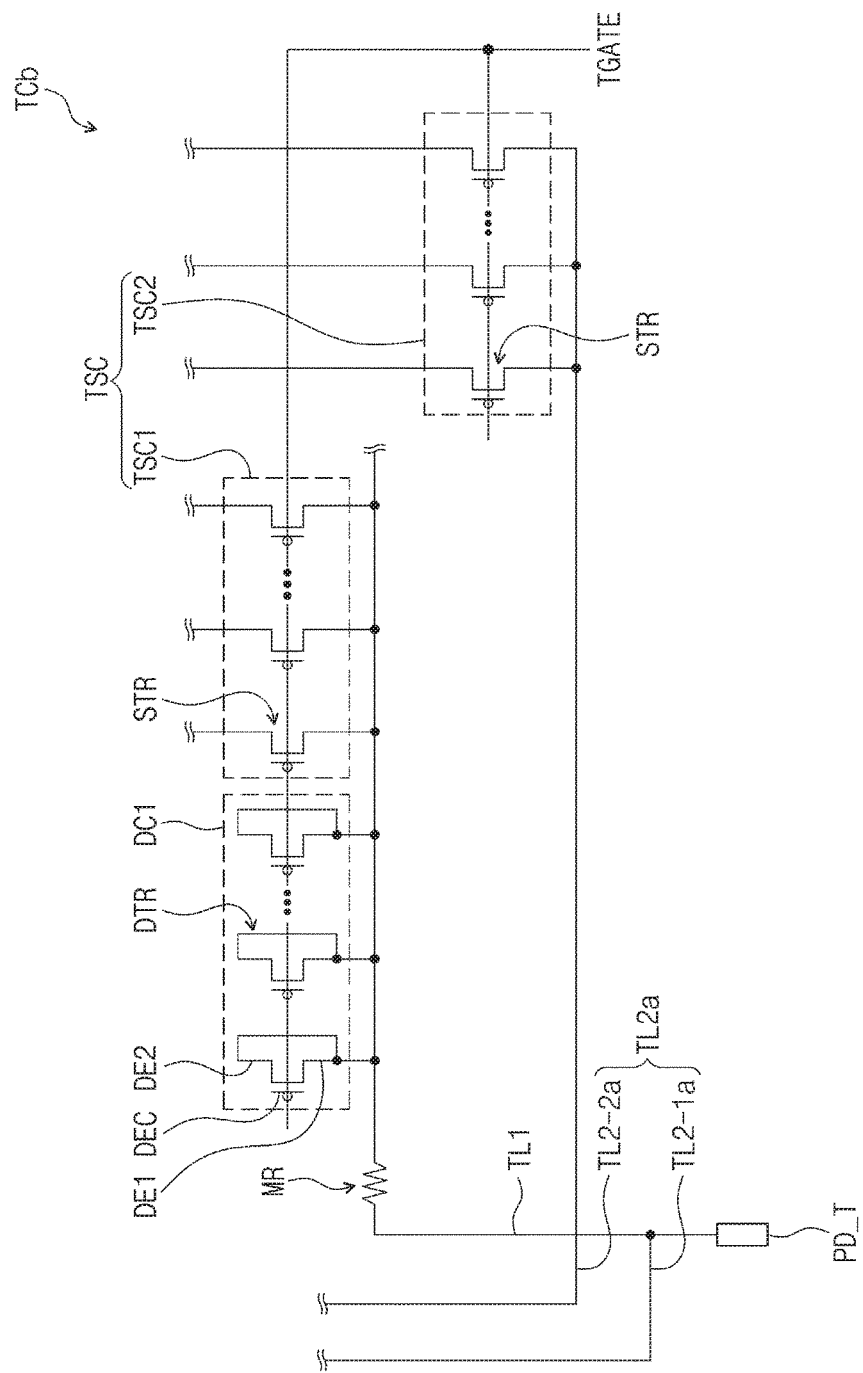
FIG. 6 is an equivalent circuit diagram showing an inspection circuit according to another exemplary embodiment of the present disclosure.

FIG. 6 is an equivalent circuit diagram showing an inspection circuit TCb according to another exemplary embodiment of the present disclosure.

When compared with FIGS. 3A and 3B, the second dummy circuits DC2a and DC2b (refer to FIGS. 3A and 3B) may be omitted from the inspection circuit TCb shown in FIG. 6.

The static electricity may flow through the inspection voltage pad PD_T. The first inspection line TL1 may provide an electrical path to the switching part TSC that is shorter than an electrical path of the second inspection line TL2a. Accordingly, the inspection circuit TCb may include only the first dummy circuit DC1 omitting the second dummy circuits DC2a and DC2b.

The static electricity flowing through the first inspection line TL1 from the inspection voltage pad PD_T may enter the first dummy circuit DC1 before entering the first switching part TSC1, thereby preventing a damage to the first switching part TSC1 due to the static electricity.

As described above, exemplary embodiments have been disclosed in the drawings and the specification. Although specific terms have been used herein, these are only intended to describe the present embodiments and are not intended to limit the meanings of the terms or to restrict the scope of the accompanying claims. Accordingly, those skilled in the art will appreciate that various modifications and other equivalent embodiments are possible from the above embodiments. Therefore, the scope of the claims should be defined by the technical spirit of the specification.

What is claimed is:

1. A display device comprising:
   a display panel comprising a display area, a non-display area disposed around the display area, and a plurality of pixels disposed in the display area;
   a first inspection line disposed in the non-display area and electrically connected to a first pixel group among the plurality of pixels;
   a second inspection line passing through a portion of the non-display area and electrically connected to a second pixel group that is different from the first pixel group among the plurality of pixels; and
   an inspection circuit disposed in the non-display area and connecting the first inspection line to the first pixel group and connecting the second inspection line to the second pixel group,
   wherein the inspection circuit comprises:
   a switching part comprising a first switching part that controls a connection between the first inspection line and the first pixel group and a second switching part that controls a connection between the second inspection line and the second pixel group; and
   a dummy circuit comprising a dummy transistor that is electrically connected to the switching part and comprising a first dummy electrode, a second dummy electrode that is connected to the first dummy electrode, and a dummy control electrode.

2. The display device of claim 1, wherein the dummy circuit comprises:
   a first dummy circuit connected between the first switching part and the first inspection line; and
   a second dummy circuit connected between the second switching part and the second inspection line.

3. The display device of claim 1, wherein the dummy circuit is connected between the first switching part and the first inspection line or between the second switching part and the second inspection line.

4. The display device of claim 1, wherein each of the first switching part and the second switching part comprises a switching transistor, the switching transistor comprises a switching control electrode, a first switching electrode that is connected to the first inspection line or the second inspection line, and a second switching electrode that is connected to the first pixel group or the second pixel group, the dummy control electrode and the switching control electrode receive a same signal, and the first dummy electrode and the second dummy electrode are connected to the first inspection line or the second inspection line.

5. The display device of claim 1, wherein the plurality of pixels comprise a first pixel displaying a first color, a second pixel displaying a second color that is different from the first color, and a third pixel displaying a third color that is different from the first color and the second color, the first pixel group comprises at least one pixel among the first, second, and third pixels, and the second pixel group comprises a pixel displaying a same color as the first pixel group.

6. The display device of claim 1, wherein each of the first pixel group and the second pixel group is provided in a plural number, the first inspection line is electrically connected to the first pixel groups, and the second inspection line is electrically connected to the second pixel groups.

7. The display device of claim 1, further comprising an inspection voltage pad to apply an inspection voltage to each of the first inspection line and the second inspection line, wherein the first inspection line is electrically connected to the inspection voltage pad and the first switching part, and the second inspection line is electrically connected to the inspection voltage pad and the second switching part.

8. The display device of claim 7, wherein the second inspection line comprises:
 a first sub-inspection line extending from the inspection voltage pad and passing through a portion of the non-display area; and
 a second sub-inspection line extending from the first sub-inspection line and connected to the second switching part.

9. The display device of claim 7, wherein the first inspection line comprises a matching resistor reducing a difference between a first voltage that is applied to the first pixel group through the first inspection line and a second voltage that is applied to the second pixel group through the second inspection line.

10. The display device of claim 9, wherein the matching resistor is provided between the inspection voltage pad and the first switching part.

11. The display device of claim 1, further comprising a plurality of pads arranged in the non-display area and receiving a data voltage applied to the plurality of pixels, wherein the inspection circuit is disposed between the display area and the plurality of pads when viewed in a plan view.

12. A display device comprising:
 a display panel comprising a display area, a non-display area surrounding the display area, and a plurality of pixels disposed in the display area;
 an inspection line electrically connected to one or more pixels among the plurality of pixels;
 a switching transistor disposed in the non-display area to control a connection between the inspection line and the one or more pixels among the plurality of pixels; and
 a dummy transistor disposed in the non-display area and connected to the inspection line, wherein the switching transistor comprises a switching control electrode, a first switching electrode that is electrically connected to the inspection line, and a second switching electrode that is electrically connected to the one or more pixels among the plurality of pixels, and the dummy transistor comprises a dummy control electrode receiving a same signal as the switching control electrode, a first dummy electrode that is electrically connected to the inspection line, and a second dummy electrode that is electrically connected to the inspection line.

13. The display device of claim 12, wherein the inspection line is provided in a plural number, the inspection lines comprise:
 a first inspection line electrically connected to a first pixel group among the plurality of pixels; and
 a second inspection line electrically connected to a second pixel group among the plurality of pixels after passing through a portion of the non-display area, and the first pixel group and the second pixel group display a same color.

14. The display device of claim 12, wherein the first dummy electrode and the second dummy electrode are connected to each other.

15. A display device comprising:
 a display panel comprising a display area, a non-display area surrounding the display area, a plurality of first pixel groups each comprising a plurality of pixels arranged in a first direction and being arranged in a second direction that crosses the first direction, and a plurality of second pixel groups each comprising a plurality of pixels arranged in the first direction and being arranged in the second direction;
 a first inspection line electrically connected to the plurality of first pixel groups;
 a second inspection line electrically connected to the plurality of second pixel groups after passing through a portion of the non-display area; and
 an inspection circuit disposed in the non-display area and connecting the first inspection line to the first pixel groups and connecting the second inspection line to the second pixel groups,
 wherein the inspection circuit comprises:
 a switching part comprising a first switching part that controls a connection between the first inspection line to the plurality of first pixel groups and a second switching part that controls a connection between the second inspection line to the plurality of second pixel groups; and
 a dummy circuit electrically connected to the switching part.

16. The display device of claim 15, wherein the dummy circuit comprises:
 a first dummy circuit connected between the first switching part and the first inspection line; and
 a second dummy circuit connected between the second switching part and the second inspection line.

17. The display device of claim 16, further comprising an inspection pad part to apply an inspection voltage to the first inspection line and the second inspection line, the first inspection line further comprises a matching resistor, and the matching resistor is provided between the inspection pad part and the first dummy circuit.

18. The display device of claim 15, wherein the dummy circuit comprises a dummy transistor, and the dummy transistor comprises a dummy control electrode receiving a same signal as a signal used to control the first switching part and the second switching part, a first dummy electrode connected to the first inspection line or the second inspection line, and a second dummy electrode connected to the first dummy electrode.

19. The display device of claim 15, wherein the plurality of first pixel groups are alternately arranged with the plurality of second pixel groups.

20. The display device of claim 15, wherein the plurality of first pixel groups and the plurality of second pixel groups display a same color.

* * * * *